(12) United States Patent
Hoshino et al.

(10) Patent No.: US 7,598,066 B2
(45) Date of Patent: Oct. 6, 2009

(54) GENE ENCODING VITAMIN $B_6$ PHOSPHATE PHOSPHATASE AND USE THEREOF

(75) Inventors: Tatsuo Hoshino, Kanagawa (JP); Yoshie Nagahashi, Kanagawa (JP); Masaaki Tazoe, Kanagawa (JP)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/528,845

(22) PCT Filed: Sep. 23, 2003

(86) PCT No.: PCT/EP03/10575

§ 371 (c)(1),
(2), (4) Date: Jan. 17, 2006

(87) PCT Pub. No.: WO2004/029252

PCT Pub. Date: Apr. 8, 2004

(65) Prior Publication Data

US 2006/0263862 A1  Nov. 23, 2006

(30) Foreign Application Priority Data

Sep. 27, 2002 (EP) ................ 02021622

(51) Int. Cl.
| | |
|---|---|
| C12N 9/16 | (2006.01) |
| C12N 15/70 | (2006.01) |
| C12N 1/21 | (2006.01) |
| C12N 1/16 | (2006.01) |
| C12P 21/06 | (2006.01) |
| C12P 17/00 | (2006.01) |
| C12P 17/12 | (2006.01) |
| C07H 21/04 | (2006.01) |

(52) U.S. Cl. .............. 435/196; 435/117; 435/122; 435/320.1; 435/252.33; 435/254.2; 536/23.2

(58) Field of Classification Search .......... 435/196, 435/69.1, 320.1, 252.3, 252.33, 488; 536/23.2
See application file for complete search history.

(56) References Cited

FOREIGN PATENT DOCUMENTS

| | | |
|---|---|---|
| EP | 0 950 715 A2 | 10/1999 |
| WO | WO 03/000875 | 1/2003 |

OTHER PUBLICATIONS

Capela et al. GenBank Accession No. Q92SG4, created Dec. 1, 2001.*
Jang et al. Human pyridoxal phosphatase. Molecular cloning, functional expression, and tissue distribution. J Biol Chem. Dec 12, 2003;278(50):50040-6. Epub Sep 30, 2003.*
Tazoe, M. et al., "Production of Vitamin $B_6$ in Rhizobium," Biosci. Biotechnol. Biochem. v. 63, No. 8, pp. 1378-1382 (1999).
Tazoe, M. et al.,"Biosynthesis of Vitamin $B_6$ in Rhizobium," J. Biol. Chem., v. 275, No. 15, pp. 11300-11305 (2000).
Capela, D. et al. "Analysis of the Chromosome Sequence of the Legume Symbiont Sinorhizobium meliloti Strain 1021," Proc. Natl. Acad. Sci., v. 98, No. 17, pp. 9877-9882 (2001). EBI Database Abstract No. XP-002275874.
Yang, Y. et al., "Involvement of the gapA- and epd (gapB)-Encoded Dehydrogenases in Pyridoxal 5'-Phosphate Coenzyme Biosynthesis in Escherichia coli K-12," J. Bacteriol., v. 180, No. 16, pp. 4294-4299 (1998).

* cited by examiner

*Primary Examiner*—Nashaat T Nashed
*Assistant Examiner*—Iqbal H Chowdhury
(74) *Attorney, Agent, or Firm*—Bryan Cave LLP

(57) ABSTRACT

Disclosed is an isolated DNA encoding vitamin $B_6$ phosphate phosphatase selected from the group consisting of: (a) a DNA sequence represented in SEQ ID NO:9; (b) a DNA sequence which encodes a polypeptide having vitamin $B_6$ phosphate phosphatase activity and hybridizes under standard conditions to the DNA sequence defined in (a) or a fragment of thereof; (c) a DNA sequence which encodes a polypeptide having vitamin $B_6$ phosphate phosphatase activity, wherein said polypeptide is at least 70% identical to the amino acid sequence represented in SEQ ID NO:10; (d) a DNA sequence which encodes a polypeptide having vitamin $B_6$ phosphate phosphatase activity and is at least 70% identical to the DNA sequence represented in SEQ ID NO:9; (e) a degenerate DNA sequence of any one of (a) to (c).

16 Claims, 3 Drawing Sheets

GENE ENCODING VITAMIN B$_6$ PHOSPHATE PHOSPHATASE AND USE THEREOF

This application is the Nation Stage of International Application NO. PCT/EP2003/01575, filed Sep. 23, 2003.

The present invention relates to a novel vitamin B$_6$ phosphate phosphatase (VB6P phosphatase) gene, recombinant microorganisms transformed with a vector having the gene, and a polypeptide having VB6P phosphatase activity. The present invention also relates to a process for preparing vitamin B$_6$ from VB6P using the recombinant microorganisms or the polypeptide.

"Vitamin B$_6$" as used in this invention includes pyridoxol (referred to as PN hereinafter), pyridoxal and pyridoxamine. Vitamin B$_6$ is a vitamin indispensable to human beings or other animals and used as a raw material of medicine or as feed additives.

The present invention provides recombinant microorganisms transformed with a novel VB6P phosphatase gene (namely pdxP), which is cloned from *Sinorhizobium meliloti*.

The present invention further provides a process for producing vitamin B$_6$ from VB6P by using a cell-free extract (referred to as CFE hereinafter) of the microorganisms and contacting VB6P with (i) the CFE, or (ii) enzyme preparation further purified from the above CFE in the presence of Mn$^{2+}$, Mg$^{2+}$, Co$^2$+, Sn$^{2+}$ or Ni$^{2+}$, and isolating the resulting vitamin B$_6$ from the reaction mixture.

The present invention provides an isolated deoxyribonucleic acid (DNA) encoding VB6P phosphatase and recombinant microorganisms which are capable of producing vitamin B$_6$ from VB6P by introducing vectors having the isolated DNA.

A VB6P phosphatase gene (pdxP) referred to herein means the gene encoding a VB6P phosphatase catalyzing dephosphorylation of VB6P to vitamin B$_6$ with high substrate specificity on pyridoxol phosphate and pyridoxal phosphate.

The term "isolated", when applied to DNA, denotes that the DNA has been removed from its natural genetic environment and is thus free of other extraneous or undesired coding sequences, and is in a form suitable for use within genetically engineered protein production systems. The term "an isolated DNA" is alternatively be termed "a cloned DNA".

The term "vector" as used herein refers to a DNA molecule, linear or circular, which are generally derived from plasmid or viral DNA, or may contain elements of both. The vector may be one which is independent of chromosome replication, or one which, when introduced into a host cell, is integrated into the host cell genome and replicated together with the choromosome(s) which it has been integrated.

The term "recombinant microorganism" refers to any microorganism transformed with a vector comprising the isolated DNA of interest. The recombinant microorganisms of the present invention express a gene encoding VB6P phosphatase for the preparation of vitamin B$_6$ from VB6P.

Cloning of the VB6P Phosphatase Gene

Figure 1:
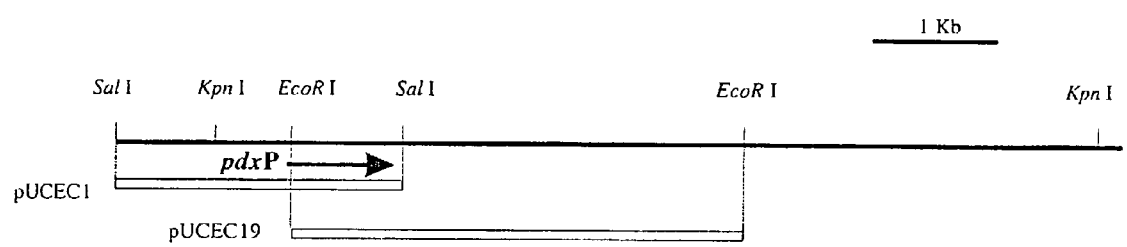
FIG. 1 shows the restriction map of chromosomal DNA around pdxP.

Purified protein of VB6P phosphatase of *S. meliloti*, e.g., is digested with a suitable protease such as trypsin and the resultant peptides are fractionated by using high pressure liquid chromatography (HPLC). Amino acid sequences of the peptides are determined by using a protein sequencer and degenerate primers are synthesized based on the amino acid sequences of the peptides. A partial fragment of VB6P phosphatase gene is obtained by PCR with the degenerate primers. A full length of VB6P phosphate gene is obtained by screening of genomic library by using the resulting partial fragment as a probe.

An example for a suitable DNA fragment is derived from *S. meliloti*, the nucleotide sequence being illustrated as SEQ ID NO:9.

In case of *S. meliloti*, the complete genome sequence has been published (EMBL accession No. AL 591688) and the BLAST search shows that the DNA sequence of pdxP of *S. meliloti* represented in SEQ ID NO:9 corresponds to the region 472329-473036, complement, open reading frame SMc01730, in accession No. AL 591688 (EMBL) except for one nucleotide substitution, i.e. the nucleotide at position 163, but the function of polypeptide represented in this open reading frame Smc01730 has not been identified before.

A functional equivalent of the *S. meliloti* pdxP can be isolated from any organism, such as, but not limited to, *Mesorhizobium loti*, other bacteria, yeast, and plant.

The present invention provides DNA sequences encoding a VB6P phosphatase, as represented in SEQ ID NO:9 as well as DNA sequences which hybridize under standard conditions with the sequences represented in SEQ ID NO:9 or fragments thereof.

The term "DNA sequences which hybridize under standard conditions" as described herein refers to DNA obtainable by using colony hybridization, plaque hybridization or Southern hybridization wherein any DNA sequence shown in SEQ ID NO:9 is used as a probe.

"Standard conditions" for hybridization mean in this context the conditions which are generally used by a person skilled in the art to detect specific hybridization signals, or preferably so called stringent hybridization and non-stringent washing conditions or more preferably so called moderately stringent conditions or even more preferably so called stringent hybridization and stringent washing conditions a person skilled in the art is familiar with. A specific example thereof is DNA which can be identified by subjecting it to hybridization using the digoxigenin (referred to as DIG hereinafter) DNA Labeling and detection kit (Roche Diagnostics, Tokyo, Japan) following the protocol given by the manufacturer. The hybridization solution contains 50% formamide, 5×SSC (10× SSC is composed of 87.65 g of NaCl and 44.1 g of sodium citrate in 1 liter), 2% blocking reagent (Roche Diagnostics, Tokyo, Japan), 0.1% N-lauroylsarcosine, and 0.3% sodium dodecyl sulfate (referred as to SDS hereinafter). Hybridization can be done overnight at 42° C. and then washing twice in 2×SSC containing 0.1% SDS for 5 min at room temperature and twice in 0.1×SSC containing 0.1% SDS for 15 min at 50° C. to 68° C. Detection can be done as indicated by manufacturer.

The present invention also includes DNA sequences which are at least 70%, preferably at least 80%, and particularly preferably more than 90% identical to the DNA sequence of SEQ ID NO:9 or a fragment thereof.

Host Cells and Vectors

Suitable host cells for the recombinant production of vitamin $B_6$ from VB6P by the expression of VB6P phosphatase may be either prokaryotic or eukaryotic and will be limited only by their ability to express active enzymes. In one embodiment, the recombinant *Escherichia coli* is provided in the present invention. As a host strain, any strains belonging to the genus *Escherichia* can be used, and the microorganisms belonging to the genus *Escherichia* may be isolated from natural sources, or may be purchased from culture collections. Preferably, *E. coli* JM109 (Takara, Shiga, Japan) can be used for the present invention. Suitable vectors which can be maintained in *E. coli* and used for expression of recombinant DNA in *E. coli* include, but not limited to, pUC series plasmids, pBR322 and its derivatives such as pKK223-3.

In another embodiment, the recombinant *S. meliloti* is provided in the present invention. As a host strain, any strain belonging to the genus *Sinorhizobium* can be used, and the microorganisms belonging to the genus *Sinorhizobium* may be isolated from natural sources, or may be purchased from culture collections. Preferably, *S. meliloti* IFO 14782 (DSM 10226) can be used for the present invention. As a vector for expression of recombinant DNA in *S. meliloti*, a broad-host range vector, such as pVK100, pRK290, pLAFR1 or RSF1010, can be used. A plasmid expressing recombinant protein in *S. meliloti* can be provided by inserting a DNA fragment encoding a promoter functioning in *S. meliloti*, such as ptac, plac, ptrc, pS1 (promoter of small ribosomal subunit of *S. meliloti*), or pNm (promoter of neomycin resistant gene).

A recombinant plasmid for incorporating pdxP can be introduced into *S. meliloti* IFO 14782 by tri-parental mating in the following manner. *S. meliloti* as a recipient strain, *E. coli* harboring helper plasmid as a helper strain, and *E. coli* harboring donor plasmid as a donor strain are cultivated separately and mixed together. After mixed cultivation on plate, *S. meliloti* receiving a recombinant plasmid can be selected on agar plate containing appropriate antibiotics. The recombinant strain carrying the plasmids is selected by the preparation of plasmid from the colonies grown on the plates and examination by endonuclease digestion.

The procedure for constructing recombinant vectors can be performed according to standard techniques known in the art. In this invention, pdxP is placed in pKK223-3 under the control of ptac promoter to construct pKKpdxP as an expression vector in *E. coli*. In another embodiment, pdxP is placed in pVK100 under the control of ptac promoter to construct pVKptacpdxP as an expression vector in *S. meliloti*.

Polypeptides

The present invention also provides polypeptides having VB6P phosphatase activity and functional derivatives of the polypeptides. Such functional derivatives are defined on the basis of the amino acid sequences of the present invention by addition, deletion and/or substitution of one or more amino acid residues of such sequences wherein such derivatives still have the VB6P phosphatase activity. Such functional derivatives can be made either by chemical peptide synthesis known in the art or by recombinant means on the basis of the DNA sequence as disclosed herein by methods known in the state of the art. Amino acid exchanges in proteins and peptides which do not generally alter the activity of such molecules are known in the state of the art. The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

Furthermore, polypeptides according to the invention include a polypeptide according to m SEQ ID NO:10, in particular those with the biological activity of VB6P phosphatase, and also those which are at least 70%, preferably at least 80%, and particularly preferably more than 90% identical to the polypeptide according to SEQ ID NO:10 and have the activity mentioned.

Production of Vitamin $B_6$ from VB6P

The recombinant microorganisms obtained in the present invention may be incubated in a medium containing an assimilable carbon source, a digestible nitrogen source, an inorganic salt, and other nutrients necessary for their growth. As a carbon source, e.g., glucose, fructose, lactose, maltose, galactose, sucrose, starch, dextrin, or glycerol may be employed. As a nitrogen source, e.g., peptone, corn steep liquor, soybean powder, yeast extract, meat extract, ammonium chloride, ammonium sulfate, ammonium nitrate, urea, or their mixture thereof may be employed. Further, for trace elements, sulfates, hydrochlorides, or phosphates of calcium, magnesium, zinc, manganese, cobalt, and iron may be employed. And, if necessary, conventional nutrient factors, a trapping agent of phosphate ion, or an antifoaming agent, such as magnesium carbonate, aluminum oxide, allophane, animal oil, vegetable oil, or mineral oil can also be added supplementary in a fermentation medium. The pH of the culture medium may be about 5.0 to about 9.0. The cultivation temperature may be in a range of from about 5° C. to about 45° C. The cultivation time may be about 1 day to about 15 days. In the cultivation, aeration and agitation usually give favorable results.

The protein having VB6P phosphatase activity may be used in the form of the culture itself which has been prepared in the above described manner, a cell-free extract (CFE) from the culture, isolated protein from the CFE, or an immobilized enzyme, to prepare vitamin $B_6$ from VB6P. The expression of the pdxP incorporated into the plasmid in suitable host cells can be analyzed by preparing CFE from the culture of recombinant microorganisms and subjecting it to SDS-polyacrylamide gel electrophoresis (SDS-PAGE). Enzymatic production for preparing vitamin $B_6$ from VB6P can be achieved by bringing the enzymatically active protein into contact VB6P in an aqueous medium. The aqueous medium can be an aqueous solution, which may be buffered, if necessary. VB6P is dissolved in water and added to the aqueous medium. Production of vitamin $B_6$ from VB6P, can be achieved in the aqueous medium with pH range between 5.5-9.0, preferably 7.0-8.0 and in a temperature range of from 15° C. to 45° C., preferably 30° C. to 40° C. for 15 min to 5 hours in the presence of $Mn^{2+}$, $Mg^{2+}$, $Co^{2+}$, $Sn^{2+}$ or $Ni^{2+}$.

After production of vitamin $B_6$ from VB6P, the produced vitamin $B_6$ may be separated from the reaction mixture and purified. For this purpose a process generally used for extracting a certain product from the reaction mixture may be applied by utilizing various properties of vitamin $B_6$. For example, the proteins may be denatured by heating or by adding a denaturant such as methanol or ethanol, and removed from the reaction mixture by filtration. The desired substance in the filtrate may be absorbed on active carbon, then eluted and purified further with an ion exchange resin. Alternatively, the filtrate may be applied directly to an ion exchange resin and, after the elution, the desired product may be recrystallized from mixture of alcohol and water. The amount of vitamin $B_6$ produced in reaction mixture can be quantified by HPLC.

The present invention will be explained more in detail by referring to the following examples.

General Methods

S. meliloti IFO 14782 was used as a source of chromosomal DNA for gene cloning experiment and as a host strain for production of vitamin $B_6$ from VB6P by transconjugants. Derivatives of E. coli K-12 were also used as a host strain for molecular cloning experiments and for production of vitamin $B_6$ from VB6P. E. coli strains were cultured in LB medium (referred to as LB hereinafter) consisting of 1% Bacto Tryptone (Becton Dickinson Microbiology systems, Md., USA), 0.5% Bacto Yeast extract (Becton Dickinson Microbiology systems, Md., USA), and 0.5% NaCl, and S. meliloti strains were cultured in LB supplemented with 0.061% $MgSO_4.7H_2O$ and 0.036% $CaCl_2.2H_2O$ (referred to as LBMC hereinafter). Bacto agar (1.5%) was added to the media for preparing agar plates. Plasmid DNA was isolated from E. coli or S. meliloti with QIAGEN Midi kit (QIAGEN GmbH, Germany) or with Automatic DNA Isolation System PI-50 (Kurabo Industry Ltd., Japan). Chromosomal DNA was isolated using QIAGEN genomic-tips.

Restriction enzymes, alkaline phosphatase, ligation kit, E. coli JM109 and HB101 competent cells (Takara Bio. Inc, Shiga, Japan), TOPO TA cloning kit (Invitrogen Japan K.K., Japan) were used according to the producer's instructions. Plasmid pKK223-3 was purchased from Amersham Biosciences Corp. For restriction enzyme analysis, the DNA fragments were fractionated in agarose gels and isolated from the gels by means of extraction using a commercially available system with QIAEXII (QIAGEN GmbH). DNA sequence was determined with an ALF DNA sequencer (Amersham Biosciences).

EXAMPLE 1

Cloning of the VB6P phosphatase gene (1) Preparation of chromosomal DNA of S. meliloti IFO 14782

S. meliloti IFO 14782 was grown in LBMC at 30° C. for 16 hours. The cells were harvested by centrifugation and chromosomal DNA was isolated by using QIAGEN genomic-tips.

(2) Acquisition of a Partial Fragment of VB6P Phosphatase Gene

To design PCR primers for cloning VB6P phosphatase gene by using degenerate PCR method, amino acid sequences of N-terminal and internal peptides were determined by using a protein sequencer, resulting in peptides Fr60 (SEQ ID NO:1), Fr64 (SEQ ID NO:2), Fr70 (SEQ ID NO:3) and N-terminal (SEQ ID NO:4).

The DNA, which encodes VB6P phosphatase of S. meliloti, was obtained by degenerate PCR method. As the forward primer, CN02 (SEQ ID NO:5) corresponding to the N-terminal amino acid sequence of VB6P phosphatase of S. meliloti (SEQ ID NO:4) was used. As the reverse primer, C642 (SEQ ID NO:6) corresponding to the internal amino acid sequence of VB6P phosphatase of S. meliloti (SEQ ID NO:2) was used.

PCR was performed according to the protocol of Takara Shuzo. Chromosomal DNA (0.1 µg) of S. meliloti IFO 14782 was used as a template, and ExTaq polymerase was used as PCR polymerase. PCR condition was as follows; 5 min at 94° C., 30 cycles of 30 seconds at 94° C., 30 seconds at 50° C., 30 seconds at 72° C., 7 min at 72° C. After the reaction, an aliquot was analyzed by agarose gel electrophoresis on 1.5% (w/v) gels and about 0.5-kb products were purified by using QIAEXII and cloned into pCR2.ITOPO. DNA sequencing of three independent clones having expected inserts was performed and it was confirmed that DNA sequences of the insert fragment of the three clones were almost identical and deduced amino acid sequences obtained from the DNA sequences contained all of amino acid sequences SEQ ID NO: 1, 2, 3 and 4. One of the clones, phoC28 was used for the next study. Next, PCR primers C101 (sense primer) (SEQ ID NO:7) and C102 (antisense primer) (SEQ ID NO:8) were synthesized based on the DNA sequence of insert fragment of phoC28 to obtain a partial fragment of VB6P phosphatase gene by PCR.

PCR condition was as follows; 5 min at 94° C., 30 cycles of 30 seconds at 94° C., 30 seconds at 55° C., 30 seconds at 72° C., 7 min at 72° C. Chromosomal DNA (0.1 µg) of S. meliloti IFO 14782 and ExTaq polymerase were used as a template and PCR polymerase, respectively. About 0.5-kb products were amplified by PCR as expected and the products were cloned into pCR2.1TOPO. As a result of DNA sequencing analysis, it was confirmed that several clones, which had identical sequences with phoC28, were obtained. One of the clones, pC1 was used for the next test, which had a partial fragment of VB6P phosphatase gene of S. meliloti IFO 14782.

(3) Southern Hybridization Analysis of S. meliloti chromosomal digests 0.5-kb EcoR I fragments of pC1 was labeled with DIG-11-dUTP by using DIG DNA labeling kit and used as a probe for Southern hybridization analysis to determine suitable restriction enzyme to use to construct genomic library. Southern hybridization analysis was performed according to the following protocol. Chromosomal DNA (3.4 µg) was digested with restriction enzymes and subjected to agarose gel electrophoresis on 0.8% (w/v) gels. The DNA was transferred to nylon membrane in 10×SSC by using Vacuum Blotter (Model 785 Bio-Rad). The membrane was prehybridized in hybridization buffer [50% formamide, 5×SSC, 2% blocking reagent, 0.1% N-lauroylsarcosine, and 0.3% SDS] for 6 hours and after addition of denatured probe overnight at 42° C. The blot was washed twice in 2×SSC containing 0.1% SDS for 5 min at room temperature and twice in 0.1×SSC containing 0.1% SDS for 15 min at 68° C. DNA fragments, which hybridized to the probe, were detected by using DIG detection kit. As a result, the probe hybridized to 2.3kb Sal I, 3.5-kb EcoR I and 7.0-kb Kpn I DNA fragments in Southern hybridization analysis of S. meliloti chromosomal digests.

(4) Construction of Genomic Library of S. meliloti IFO 14782

The chromosomal DNA was partially digested with EcoR I subjected to agarose gel electrophoresis. The 15- to 30-kb DNA fragments were recovered from the gels and ligated into pVK100, which was digested with EcoR I and dephosphorylated with bacterial alkaline phosphatase. The ligation mixture was used for the in vitro packaging reaction and the phage particles were used to infect E. coli 8767 cells at the log phase of growth. The cell suspension was plated onto LB plate containing 10 µg/ml of tetracycline (referred to as Tc hereinafter). The colonies resistant to Tc were obtained and stocked as genomic library of S. meliloti IFO 14782.

(5) Screening of Genomic Library of S. meliloti IFO 14782

To screen colonies having the VB6P phosphatase gene of S. meliloti from the library prepared in Example 1-(4), the colonies grown on LB plate with 10 µg/ml of Tc were transferred to the nylon transfer membrane (Hybond™-N⁺ Amersham Pharmacia Biotech) and subjected to colony hybridization with the probe prepared in Example 1-(3). Among 3000 clones of the genomic library of *S. meliloti* IFO 14782, seven positive colonies were obtained. Plasmids were prepared by using QIAGEN-midi tip from the positive colonies, and digested with restriction enzymes, EcoR I and Sal I. The digested plasmids were subjected to agarose gel electrophoresis on 1.0% (w/v) gels and Southern hybridization analysis was performed as described in Example 1-(3) and it was confirmed that the probe was hybridized to 2.3-kb of Sal I and 3.5-kb EcoR I fragments of digested plasmids. One of the plasmids from positive colonies, which have about 24-kb EcoR I fragment, was named pVEC1.

(6) Sequencing of VB6P Phosphatase Gene 2.3-kb Sal I and 3.5-kb EcoR I fragments of pVEC1 were ligated into pUC19 and obtained plasmids were named pUCEC1 and pUCEC19, respectively. The nucleotide sequence of the insert fragment of pUCEC1 and pUCEC19 was determined with an ALF DNA sequencer. As a result of the DNA sequencing, 708-bp sequence encoded ORF consisting of 235 amino acids, which contains all amino acid sequences SEQ ID NO:1, 2, 3 and 4, was observed. This result showed that the 708-bp sequence as shown in SEQ ID NO:9, corresponded to VB6P phosphatase gene, and this gene was named pdxP. The restriction map of m chromosomal DNA around pdxP is shown in FIG. 1.

EXAMPLE 2

Expression of pdxP and Production of Vitamin $B_6$ from VB6P (1) Expression of pdxP in *E. coli*

To express the pdxP gene under the control of the tac promoter in *E. coli*, the plasmid pKKpdxP was constructed. The pdxP gene was amplified from 100 ng of chromosomal DNA of *S. meliloti* IFO 14782 by advantage-HF PCR kit (Clontech, USA) using 10-pmol of the primers, Primer P101 (SEQ ID NO: 11) and Primer P102 (SEQ ID NO: 12).

The reaction conditions were as follows: after holding 15 seconds at 94° C., 30 cycles of 15 seconds at 94° C., 4 min at 68° C. The reaction mixture was subjected to agarose gel electrophoresis and a 0.86-kb DNA fragment was recovered from the gels with QIAEXII. The obtained 0.86-kb fragment was cloned in pCRII-TOPO vector by TOPO TA cloning kit, and the obtained 5 independent candidates were examined for DNA sequence of insert fragment. As a result, one of the candidates, TOPOpdxP105, which had exact insert sequence, was used for further study.

Figure 2:
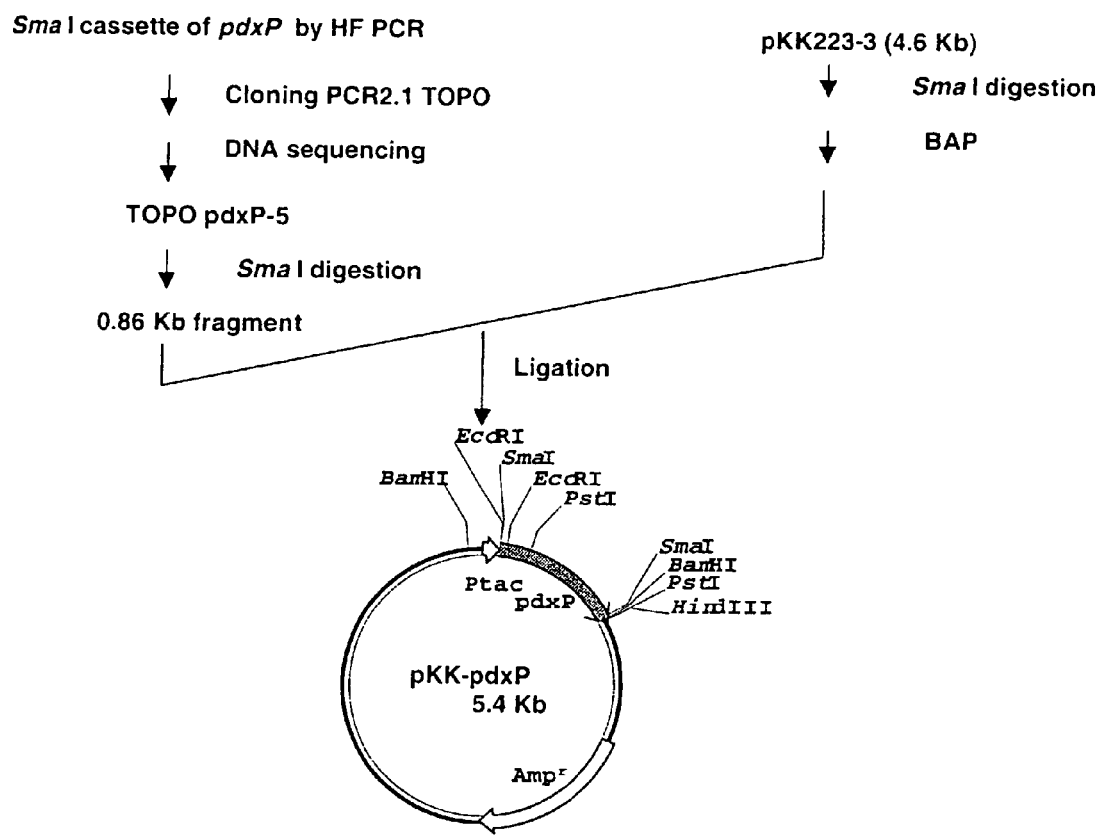
FIG. 2 shows the construction of pKK-pdxP. The pdxP gene was amplified by PCR and cloned in the pCRII-TOPO vector. The resulting plasmid was named TOPO pdxP105 (shown as TOPO pdxP-5 in the figure). A 0.86-kb Sma I fragment containing the pxdP gene from TOPO pdxP105 was ligated into Sma I site of pKK223-3 in an orientation that allows transcription of pdxP from tac promoter, and resulting plasmid was named pKK-pdxP.

0.86-kb Sma I fragment from TOPOpdxP1O5 was ligated into Sma I site of pKK223-3 in an orientation that allowed transcription of pdxP from tac promoter and resulting plasmid was named pKKpdxP (FIG. 2).

Then two independent clones JM109 having pKKpdxP (namely, JM109/pKKpdxP-1 and JM109/pKKpdxP-7) were grown in LB with 100 μg/ml ampicillin (Amp) and 1 mg/ml pyridoxamine. After 1.5-hour cultivation, the expression of pdxP was induced by adding 1 mM isopropyl-β-D-thiogalactopyranose (IPTG). After cultivation for another 4.5 hours, the cells were harvested and suspended in 20 mM Tris-HCl, pH 7.5, buffer containing 15% sucrose, 1 mM dithiothreitol (DTT), 1 mM $MnCl_2$, 1 mM $MgCl_2$, and 0.1 mM phenylmethylsulfonyl fluoride (PMSF). The cell suspension was subjected to a French press at a pressure of 800 kg/cm² and the resultant lysate was centrifuged at 35,000×g for 60 min at 4° C. to remove cell debris. The supernatant was used as the CFE after dialysis with the same buffer. To confirm the expression of PdxP, CFE was subjected to SDS-PAGE on 12.5% (w/v) gels and stained with Coomassie Brilliant Blue (Rapid Stain CBB Kit, nacalai tesque Japan). Overproduction of polypeptide with an expected molecular size (29.0 kDa) 5 was detected in *E. coli* JM109/pKKpdxP-1 but not in *E. coli* JM109/pKKpdxP-7. Then the CFE of *E. coli* JM 109/pKKpdxP-1 was used for further study.

(2) Production of Vitamin $B_6$ from VB6P in CFE of Recombinant *E. coli*

Production of vitamin $B_6$ from VB6P was done by using the CFE prepared in Example 2-(1). The reaction mixture contained 50 mM Tris-HCl buffer, pH 7.5, 2 mM pyridoxal 5'-phosphate (PNP), 1 mM $MnCl_2$ and CFE (0.5 mg protein) in 125 μl. The reaction was done at 37° C. for 15 min and the amount of PN was quantified by HPLC by the internal standard method with 4'-deoxypyridoxol as described below. To prepare the samples for HPLC, 200 μl of 100 mg/l of 4'-deoxypyridoxol as an internal substance, 50 μl of 60% perchloric acid, and 950 μl of deionized water was added to 50 μl of the standard solution of pyridoxol or the reaction mixture, and then the mixture was put on the ice for 10 min. Then the mixture was centrifuged at 15,000 rpm and the supernatant was put on the following column. The analytical conditions were as follows: column: Capcell pak C18 SG120 (4.6× 250 mm) (Shiseido Co., Ltd., Tokyo, Japan); mobile phase: 0.1 M sodium perchlorate, 0.1 M potassium phosphate, and 2% acetonitrile (pH 3.5); column temperature: 30° C.; flow rate, 1.0 ml/min; and detector: ultraviolet (at 292 nm). The result is shown in Table 5. The concentration of formed PN in the reaction mixture containing CFE of JM109/pKKpdxP was 0.50 mM and it was 1.4 times higher than that of JM109/pKK223-3 (0.37 mM).

TABLE 5

| Amount of formed PN in CFE of JM109/pKKpdxP | | |
|---|---|---|
| | Formed PN | |
| CFE | (mM) | (Ratio) |
| JM109/pKK223-3 (vector) | 0.37 | 1 |
| JM109/pKKpdxP | 0.50 | 1.4 |
| minus CFE | ND | ND |

ND: Not detectable (3) Expression of pdxP in *S. meliloti*

Figure 3:
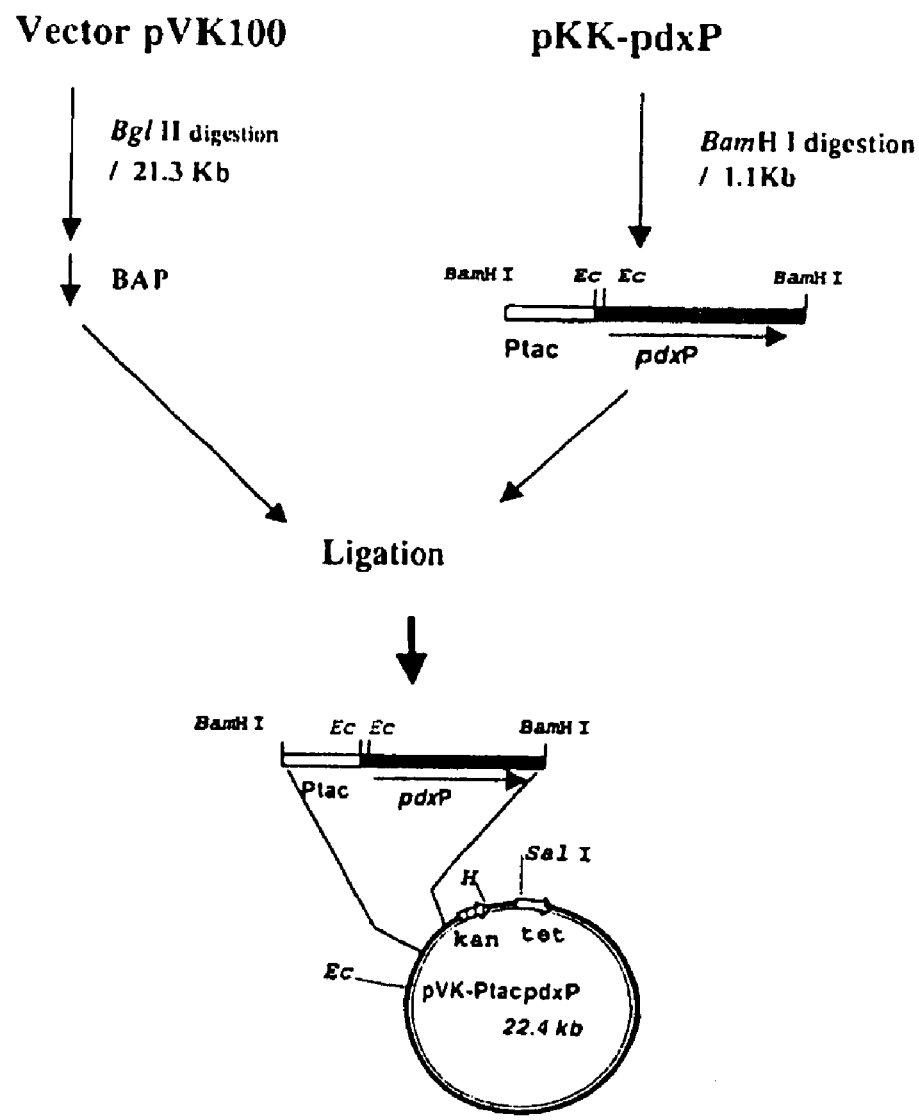
FIG. 3 shows the construction of pVK-PtacpdxP. A cosmid vector, pVK100 was digested with BgI II, then a fragment about 21.3 kb in size was recovered. After the fragment was treated with bacterial alkaline phosphatase, a 1.1-kb BamH I fragment from pKKpdxP was ligated in the BgI II digested and dephosphorylated 21.3-kb fragment to give a plasmid pVKPtacpdxP (FIG. 3).

Mobilizable cosmid pVK100 was digested with Bgl II, then about 21.3-kb fragments were recovered. After the fragments were treated with bacterial alkaline phosphatase, 1.1-kb BamH I fragments from pKKpdxP were ligated into the Bgl II digested and dephosphorylated fragment to give a plasmid pVKPtacpdxP (FIG. 3). Then *S. meliloti* IFO 14782 having pVKPtacpdxP was obtained by tri-parental conjugation, and the cells were grown in the seed medium containing 1% glucose, 0.5% polypeptone, 0.2% Bacto Yeast extract, 0.1% $KH_2PO_4$, 0.05% $MgSO_4.7H_2O$, 0.001% $MnSO_4.5H_2O$, and 0.001% $FeSO_4.7H_2O$, and seed culture was transferred into glucose-pol)Teptone medium containing 4% glucose, 2% polypeptone, 0.2% Bacto Yeast extract, 0.05% $MgSO_4.7H_2O$, 0.05% $MnSO_4.5H_2O$, and 0.001% $FeSO_4.7H_2O$, and cultivated at 30° C. for 3 days. The cells were harvested by centrifugation and washed with saline and suspended with 20 mM Tris-HCl, pH 7.5, buffer containing 15% sucrose, 1 mM DTT, 1 mM $MnCl_2$, 1 mM $MgCl_2$, and 0.1 mM PMSF. The cell suspension was subjected to a French press at a pressure of 800 kg/cm² and the resultant lysate was centrifuged at 35,000×g for 60 minutes at 4° C. to remove cell debris. The supernatant was used as CFE after dialysis with the same buffer.

(4) Production of vitamin B$_6$ from VB6P by CFE of recombinant *S. meliloti*

Production of vitamin B$_6$ from VB6P was examined by using the CFE prepared in Example 2-(3). The reaction mixture contained 50 mM Tris-HCl buffer, pH 7.5, 2 mM PNP, 1 mM MnCl$_2$, and CFE (0.4 mg protein) in 125 μl. The reaction was done at 37° C. for 30 min and the amount of PN was quantified by HPLC as shown in Example 2-(2). The result is shown in Table 6. The concentration of formed PN in reaction mixture containing CFE of *S. meliloti* IFO 14782/pVKPtacpdxP was 1.66 mM and it was 4 times higher than that of *S. meliloti* IFO 14782 (0.41 mM).

TABLE 6

Amount of formed PN in CFE of *S. meliloti* IFO 14782/pVKPtacpdxP

| CFE | Formed PN (mM) | (Ratio) |
|---|---|---|
| *S. meliloti* IFO 14782 | 0.41 | 1 |
| *S. meliloti* IFO 14782/pVKPtacpdxP | 1.66 | 4.0 |
| minus CFE | ND | ND |

ND: Not detectable

The invention claimed is:

1. A vector or plasmid comprising an isolated DNA encoding vitamin B6 phosphate phosphatase selected from the group consisting of:
   (a) the DNA sequence of SEQ ID NO:9;
   (b) a DNA sequence encoding a polypeptide having vitamin B6 phosphate phosphatase activity, which hybridizes under stringent hybridization and stringent washing conditions to the complementary DNA sequence defined in (a) wherein the stringent hybridization and stringent washing conditions comprise hybridizing in 5×SSC, 0.3% SDS, 2% blocking reagent, 0.1% N-lauroylsarcosine, 50% formamide overnight at 42° C. and washing twice in 2×SSC, 0.1% SDS at room temperature for 5 minutes and then washing twice in 0.1×SSC, 0.1% SDS at 68° C. for 15 minutes;
   (c) a DNA sequence encoding a polypeptide having vitamin B6 phosphate phosphatase activity, wherein said polypeptide is at least 90% identical to the amino acid sequence of SEQ ID NO:10; and
   (d) a DNA sequence encoding a polypeptide having vitamin B6 phosphate phosphatase activity and is at least 90% identical to the DNA sequence of SEQ ID NO:9.

2. A recombinant microorganism of the genus *Sinorhizobium* or *Escherichia*, capable of producing vitamin B6 from vitamin B6 phosphate, wherein said microorganism is transformed with a DNA encoding vitamin B6 phosphate phosphatase selected from the group consisting of:
   (a) the DNA sequence of SEQ ID NO:9;
   (b) a DNA sequence encoding a polypeptide having vitamin B6 phosphate phosphatase activity, which hybridizes under stringent hybridization and stringent washing conditions to the complementary DNA sequence defined in (a), wherein the stringent hybridization and stringent washing conditions comprise hybridizing in 5×SSC, 0.3% SDS, 2% blocking reagent, 0.1% N-lauroylsarcosine, 50% formamide overnight at 42° C. and washing twice in 2×SSC, 0.1% SDS at room temperature for 5 minutes and then washing twice in 0.1×SSC, 0.1% SDS at "68° C. for 15 minutes;
   (c) a DNA sequence encoding a polypeptide having vitamin B6 phosphate phosphatase activity, wherein said polypeptide is at least 90% identical to the amino acid sequence of SEQ ID NO:10; and
   (d) a DNA sequence encoding a polypeptide having vitamin B6 phosphate phosphatase activity and is at least 90% identical to the DNA sequence of SEQ ID NO:9.

3. The microorganism of claim 2, wherein said microorganism is *Sinorhizobium meliloti* IFO 14782 having pVKP-tacpdxP (*S. meliloti* IFO 14782/pVKPtacpdxP).

4. The microorganism of claim 2, wherein said microorganism is *Escherichia coli* JM109 having pKKpdxP (*E. coli* JM109/pKKpdxP).

5. A recombinant microorganism of the genus *Sinorhizobium* or *Escherichia*, capable of producing vitamin $B_6$ from vitamin $B_6$ phosphate, wherein said microorganism is transformed with the vector or plasmid of claim 1.

6. An isolated polynucleotide comprising the polynucleotide sequence of SEQ ID NO:9.

7. An isolated polynucleotide comprising a polynucleotide sequence that encodes the polypeptide sequence of SEQ ID NO:10.

8. A process for preparing a cell-free extract having vitamin $B_6$ phosphate phosphatase activity, which comprises cultivating the microorganism according to claim 2 wherein the microorganism is cultivated under conditions in a medium containing an assimilable carbon source, a digestible nitrogen source, inorganic salts, and other nutrients necessary for the growth of the microorganism at a pH value of about 5.0 to about 9.0, at a temperature about 5° C. to about 45° C., and for 1 day to about 15 days under aerobic conditions, and disrupting cells of the microorganism.

9. The process according to claim 8, wherein said microorganism is *Sinorhizobium meliloti* IFO 14782 having pVKP-tacpdxP (*S. meliloti* IFO 14782/pVKPtacpdxP).

10. The process according to claim 8, wherein said microorganism is *Escherichia coli* JM 109 having pKKpdxP (*E. coli* JM 109/pKKpdxP).

11. The process for producing vitamin $B_6$ from vitamin $B_6$ phosphate which comprises contacting vitamin $B_6$ phosphate with the cell-free extract of microorganism according to claim 2 in a reaction mixture, and recovering the resulting vitamin $B_6$ from the reaction mixture.

12. The process according to claim 11, wherein said microorganism is *Sinorhizobium meliloti* IFO 14782 having pVKP-tacpdxP (*S. meliloti* IFO 14782/pVKPtaccpdxP).

13. The process according to claim 11, wherein said microorganism is *Escherichia coli* JM109 having pKKpdxP (*E. coli* JM 109/pKKpdxP).

14. A process for producing vitamin $B_6$ from vitamin $B_6$ phosphate which comprises:
   (a) cultivating a recombinant microorganism according to claim 4 wherein the recombinant microorganism is cultivated under the following conditions: in a medium containing an assimilable carbon source, a digestible nitrogen source, inorganic salts, and other nutrients necessary for the growth of the microorganism at a pH value of about 5.0 to about 9.0, at a temperature about 5° C. to about 45° C., and for 1 day to about 15 days under aerobic conditions;
   (b) disrupting cells of the recombinant microorganism to produce a cell-free extract; and
   (c) contacting vitamin $B_6$ phosphate with the cell-free extract in a reaction mixture, and recovering the resulting vitamin $B_6$ from the reaction mixture.

15. The process according to claim 14, wherein said recombinant microorganism is *Sinorhizobium meliloti* IFO 14782 having pVKPtacpdxP (*S. meliloti* IFO 14782/pVKPtacpdxP).

16. The process according to claim 14, wherein said recombinant microorganism is *Escherichia coli* JM 109 having pKKpdxP (*E. coli* JM 109/pKKpdxP).

* * * * *

```
                     SEQUENCE LISTING

<160> NUMBER OF SEQ ID NOS: 12

<210> SEQ ID NO 1
    <211> LENGTH: 20
    <212> TYPE: PRT
    <213> ORGANISM: Sinorhizobium meliloti

<400> SEQUENCE: 1

Ala His Ala Ile Asp Tyr Ser Val Val Pro Ala Asp Pro Ala Leu Gly
    1               5                   10                  15

Glu Ala Ile Lys
                20

<210> SEQ ID NO 2
    <211> LENGTH: 14
    <212> TYPE: PRT
    <213> ORGANISM: Sinorhizobium meliloti

<400> SEQUENCE: 2

Ile Asp Thr Ala Asn Ala Val Met Phe Glu Asp Leu Pro Arg
    1               5                   10

<210> SEQ ID NO 3
    <211> LENGTH: 23
    <212> TYPE: PRT
    <213> ORGANISM: Sinorhizobium meliloti

<400> SEQUENCE: 3

Asp His Gly Thr Thr Leu Gln Gly Leu Met Leu His His Gly Ile Asp
    1               5                   10                  15

Pro Asn Asp Phe Leu Glu Arg
                20

<210> SEQ ID NO 4
    <211> LENGTH: 10
    <212> TYPE: PRT
    <213> ORGANISM: Sinorhizobium meliloti

<400> SEQUENCE: 4

Met Lys Lys Leu Asp Arg Met Pro Thr His
    1               5                   10

<210> SEQ ID NO 5
    <211> LENGTH: 21
    <212> TYPE: DNA
    <213> ORGANISM: Artificial Sequence
    <220> FEATURE:
```

```
<223> OTHER INFORMATION: Primer CN02
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 5
atgaaraary tngaymgnat g                                              21

<210> SEQ ID NO 6
<211> LENGTH: 20
<212> TYPE: DNA
<213> ORGANISM: Artificial Sequence
<220> FEATURE:
<223> OTHER INFORMATION: Primer C642
<220> FEATURE:
<221> NAME/KEY: misc_feature
<222> LOCATION: (12)..(12)
<223> OTHER INFORMATION: n is a, g, c or t
<220> FEATURE:
<221> NAME/KEY: misc_feature
<222> LOCATION: (15)..(15)
<223> OTHER INFORMATION: n is a, g, c or t

<400> SEQUENCE: 6
tcytcraaca tncangcrtt                                                20

<210> SEQ ID NO 7
<211> LENGTH: 21
<212> TYPE: DNA
<213> ORGANISM: Artificial Sequence
<220> FEATURE:
<223> OTHER INFORMATION: Primer C101

<400> SEQUENCE: 7
gccgaattcg cccatgtcac c                                              21

<210> SEQ ID NO 8
<211> LENGTH: 21
<212> TYPE: DNA
<213> ORGANISM: Artificial Sequence
<220> FEATURE:
<223> OTHER INFORMATION: Primer C102

<400> SEQUENCE: 8
cgccgtgtcg atgcggtgaa g                                              21

<210> SEQ ID NO 9
<211> LENGTH: 708
<212> TYPE: DNA
<213> ORGANISM: Sinorhizobium meliloti

<400> SEQUENCE: 9
atgaagaagc tcgaccgcat gccgacccac gccgaattcg cccatgtcac cgactgggtc     60
ttcgacctcg acaacacgct ctatccgcat cacgtcaatc tgttctcaca gatcgaccgc    120
aacatgacgg cctatgttgc cgaactcctg tcgctggagc ctgcggaggc gaagaagctg    180
cagaaggaat actaccgcga ccacggcacc acgcttcagg gcctgatgct tcatcacggc    240
atcgatccca tgatttcct  cgaaagagcc cacgccatcg actatagcgt ggtgccggcc    300
gatccggcgc tcggcgaggc gatcaaggcg ctgcccggac gcaagttcat cttcaccaac    360
ggcagcgtcg cccatgcgga gatgaccgcg cgggcgctcg gcattctcga gcatttcaac    420
```

```
gacatcttcg acatcgtcgc cgccggcttc ataccgaagc ccgccggcga cacctacgac    480
aagttcatgg ccttcaccg catcgacacg gcgaatgagg tgatgttcga ggatctgccg     540
cgcaacctgg tcgtccctaa ggcgctcggc atgaagacgg tgctgctcgt gccgcgcaat    600
ctcgaatacg agttcgccga ggcctgggaa acgtcgagcg acgcggacga tcagatcgac    660
tacgtcacgg aagacctggc gggtttcctg cgcagtgtga ttgtttag               708
```

```
<210> SEQ ID NO 10
<211> LENGTH: 235
<212> TYPE: PRT
<213> ORGANISM: Sinorhizobium meliloti

<400> SEQUENCE: 10

Met Lys Lys Leu Asp Arg Met Pro Thr His Ala Glu Phe Ala His Val
1               5                   10                  15

Thr Asp Trp Val Phe Asp Leu Asp Asn Thr Leu Tyr Pro His His Val
            20                  25                  30

Asn Leu Phe Ser Gln Ile Asp Arg Asn Met Thr Ala Tyr Val Ala Glu
        35                  40                  45

Leu Leu Ser Leu Glu Pro Ala Glu Ala Lys Lys Leu Gln Lys Glu Tyr
    50                  55                  60

Tyr Arg Asp His Gly Thr Thr Leu Gln Gly Leu Met Leu His His Gly
65                  70                  75                  80

Ile Asp Pro Asn Asp Phe Leu Glu Arg Ala His Ala Ile Asp Tyr Ser
                85                  90                  95

Val Val Pro Ala Asp Pro Ala Leu Gly Glu Ala Ile Lys Ala Leu Pro
            100                 105                 110

Gly Arg Lys Phe Ile Phe Thr Asn Gly Ser Val Ala His Ala Glu Met
        115                 120                 125

Thr Ala Arg Ala Leu Gly Ile Leu Glu His Phe Asn Asp Ile Phe Asp
    130                 135                 140

Ile Val Ala Ala Gly Phe Ile Pro Lys Pro Ala Gly Asp Thr Tyr Asp
145                 150                 155                 160

Lys Phe Met Gly Leu His Arg Ile Asp Thr Ala Asn Glu Val Met Phe
                165                 170                 175

Glu Asp Leu Pro Arg Asn Leu Val Val Pro Lys Ala Leu Gly Met Lys
            180                 185                 190

Thr Val Leu Leu Val Pro Arg Asn Leu Glu Tyr Glu Phe Ala Glu Ala
        195                 200                 205

Trp Glu Thr Ser Ser Asp Ala Asp Asp Gln Ile Asp Tyr Val Thr Glu
    210                 215                 220

Asp Leu Ala Gly Phe Leu Arg Ser Val Ile Val
225                 230                 235

<210> SEQ ID NO 11
<211> LENGTH: 32
<212> TYPE: DNA
<213> ORGANISM: Artificial Sequence
<220> FEATURE:
<223> OTHER INFORMATION: Primer P101

<400> SEQUENCE: 11
gaagcttccc gggccgtgtc ataaacccgc cc                                  32

<210> SEQ ID NO 12
<211> LENGTH: 32
```

```
<212> TYPE: DNA
<213> ORGANISM: Artificial Sequence
<220> FEATURE:
<223> OTHER INFORMATION: Primer P102

<400> SEQUENCE: 12
caagcttccc gggatcatcg ccgggtttta cg                                    32
```